(12) United States Patent
Jefferies

(10) Patent No.: US 8,047,841 B2
(45) Date of Patent: Nov. 1, 2011

(54) APPLICATION DENTAL MATERIALS TO THE ORAL CAVITY

(75) Inventor: Steven R. Jefferies, York, PA (US)

(73) Assignee: Dentsply International, Inc., York, PA (US)

( * ) Notice: Subject to any disclaimer, the term of this patent is extended or adjusted under 35 U.S.C. 154(b) by 517 days.

(21) Appl. No.: 11/807,503

(22) Filed: May 29, 2007

(65) Prior Publication Data

US 2007/0231772 A1     Oct. 4, 2007

(51) Int. Cl.
*A61C 5/02*     (2006.01)
*A61G 5/02*     (2006.01)

(52) U.S. Cl. .......................... 433/81; 433/224

(58) Field of Classification Search ............... 433/81, 433/224, 226, 228, 90; 401/1, 2, 4; 222/1, 222/146.1, 146.2, 196–200
See application file for complete search history.

(56) References Cited

U.S. PATENT DOCUMENTS

| | | |
|---|---|---|
| 2,531,680 A | 11/1950 | Gustafson |
| 3,280,459 A | 10/1966 | Walker et al. |
| 3,401,690 A | 9/1968 | Martin |
| 3,513,550 A | 5/1970 | Ekman |
| 3,898,739 A | 8/1975 | Gayso |
| 3,919,775 A | 11/1975 | Malmin |
| 4,204,011 A | 5/1980 | Tanabe et al. |
| 4,219,619 A | 8/1980 | Zarow |
| 4,437,606 A | 3/1984 | Graser |
| 4,634,383 A | 1/1987 | Beyer et al. |
| 4,850,875 A | 7/1989 | Takatsu |
| 4,976,625 A | 12/1990 | Weisman |
| 5,007,837 A | 4/1991 | Werly |
| 5,133,661 A | 7/1992 | Euvrard |
| 5,145,369 A | 9/1992 | Lustig et al. |
| 5,151,030 A | 9/1992 | Comeaux |
| 5,437,606 A | 8/1995 | Tsukamoto |
| 5,639,238 A | 6/1997 | Fishburne, Jr. |
| 5,839,895 A | 11/1998 | Fishburne, Jr. |
| 5,886,064 A | 3/1999 | Rheinberger et al. |
| 6,139,320 A | 10/2000 | Hahn |
| 6,224,379 B1 | 5/2001 | Abedian et al. |
| 6,312,261 B1 | 11/2001 | Mays |
| 7,014,462 B1 * | 3/2006 | Tilse .................. 433/90 |
| 2002/0058231 A1 * | 5/2002 | Friedman .............. 433/90 |

FOREIGN PATENT DOCUMENTS

| | | | |
|---|---|---|---|
| DE | 40 32 505 | | 8/1991 |
| DE | 299 12 643 | | 4/2000 |
| FR | 2 190 176 | | 1/1974 |
| WO | WO 00/47126 | | 8/2000 |
| WO | WO0117454 | * | 3/2001 |
| WO | WO 01/62174 | | 8/2001 |
| WO | WO 2004/071326 | | 8/2004 |

\* cited by examiner

*Primary Examiner* — Todd Manahan
*Assistant Examiner* — Matthew Nelson
(74) *Attorney, Agent, or Firm* — Douglas J. Hura; Leana Levin; David A Zdurne

(57) ABSTRACT

The application of a dental material to a site in the oral cavity includes the application of vibrational energy and heat to the dental material in order to substantially impart a preselected or desired viscosity to the dental material.

6 Claims, 1 Drawing Sheet

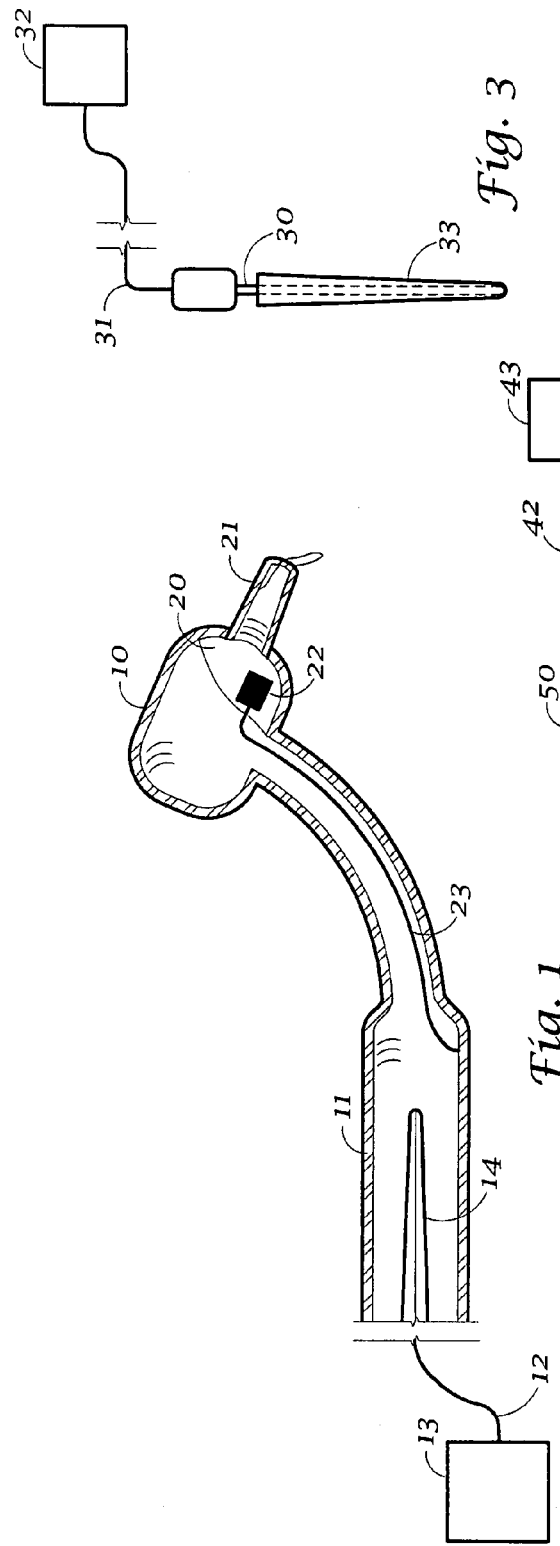
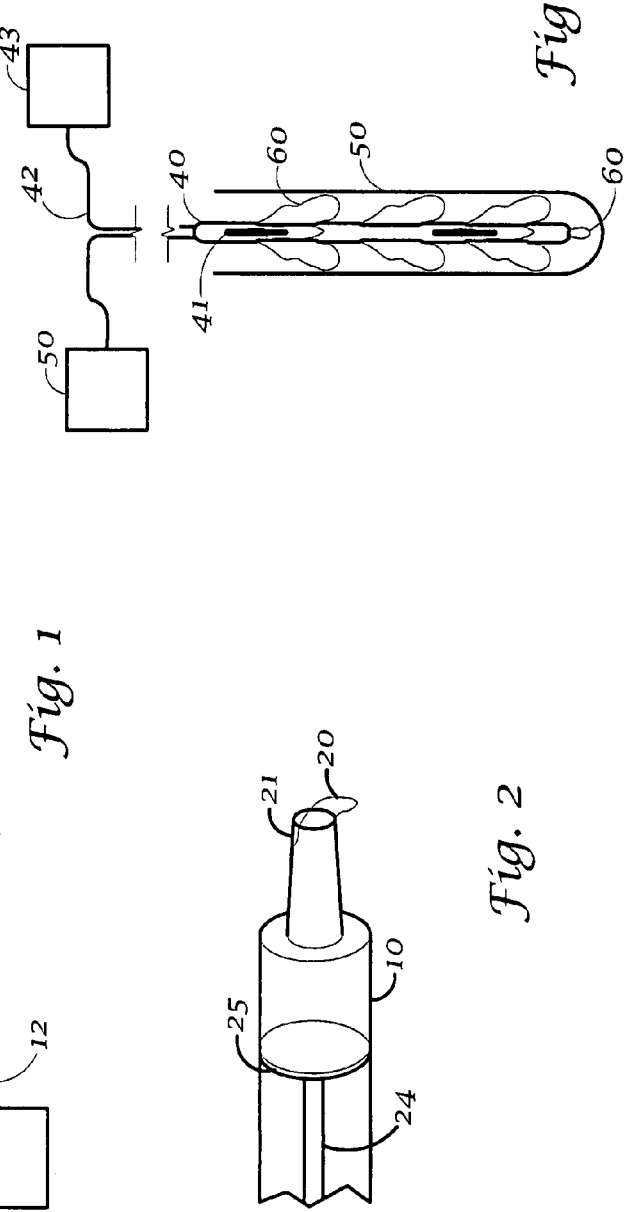

ional and experience what consistency is useful for his or her particular technique. Such viscosities will also vary between practitioners even when they use the same materials and equipment. Therefore, again, viscosity is not an absolute limitation. The operative objective of the invention is to reduce viscosity by applying heat and energy to the point where the practitioner can properly, precisely and completely place the material as desired.

APPLICATION DENTAL MATERIALS TO THE ORAL CAVITY

TECHNICAL FIELD

The present invention relates to the application of dental materials. More particularly, the invention relates to improvements in placing such materials in the oral cavity. Specifically, the invention relates to improvements in such uses while employing heat in conjunction with vibration or other mechanical actions.

BACKGROUND OF THE INVENTION

Dental professionals use a wide variety of materials in maintaining, improving or otherwise treating dental health. These include for example, dental restorative composites and amalgams, adhesives, cements, veneers, impression and registration materials, endodontic obturation materials, and the like. It is often the case that a successful dental procedure requires precise and complete application of such materials to fill spaces and voids, to flow properly, to maintain a suitable viscosity and to otherwise maintain a proper consistency for adequate handling and application by the practitioner.

The present invention provides for improvements in such techniques and the handling of such dental materials.

DISCLOSURE OF THE INVENTION

It is therefore, an object of the invention to provide for improvements in the application of dental materials to the oral cavity. The invention has a broad range of application to a variety of dental materials, but is particularly suited for the application of dental restoratives and endodontic obturation materials.

In general, the present invention imparts suitable vibrational and heat energy to the material to be applied, such that a proper viscosity is achieved allowing the material to flow from the application instrument to the site of application in the oral cavity, where it is otherwise treated in a conventional manner, such as for example, by then being cured. Optionally, other mechanical forces may be applied to move or otherwise place the dental material, such as by using a spatula, a piston, a nozzle or any other such mechanical devices providing a mechanical force upon the material to move or deliver it.

DESCRIPTION OF THE DRAWINGS

FIG. 1 is a side elevational, partially broken view of a delivery device embodying the concepts of the invention, shown for environmental purposes, as being affixed to a handpiece.

FIG. 2 is an alternative embodiment of the delivery device as in FIG. 1.

FIG. 3 is another embodiment of a delivery device according to the invention, and particularly suited for endodontic use.

FIG. 4 is an alternative embodiment of a delivery device particularly suited for endodontic use.

PREFERRED EMBODIMENTS FOR CARRYING OUT THE INVENTION

The present invention uses heat and vibration to make otherwise non-flowing or flow-resistant materials flow by reducing their viscosity. The required viscosity which must be achieved will vary depending upon the particular material being used and the dental procedure being carried out. Therefore, the viscosity reductions are not an absolute limitation of the invention. However, a practitioner will know by training and experience what consistency is useful for his or her particular technique. Such viscosities will also vary between practitioners even when they use the same materials and equipment. Therefore, again, viscosity is not an absolute limitation. The operative objective of the invention is to reduce viscosity by applying heat and energy to the point where the practitioner can properly, precisely and completely place the material as desired.

Vibrational energy is imparted by any suitable means, but is preferably imparted by operative connection of the delivery device to an ultrasonic generator. Such devices are well known in the dental art, and include for example, the CAVITRON line available from DENTSPLY INTERNATIONAL INC. of York, Pa. The actual energy supplied will vary depending upon the viscosity reduction required, which as discussed above, is not an absolute limitation of the invention.

For example, there is depicted in FIG. 1, a delivery device 10 which may be a preloaded capsule or the like, or which may be individually loaded as need by the practitioner, and which is operatively connected to a handpiece 11. Handpiece 11 is in turn connected by operative connector 12 to an ultrasonic generator 13. Handpiece 11 preferably contains elements such as magnetostrictive or piezo elements 14 for accepting energy from generator 13 and translating the energy into vibration-inducing ultrasonic energy applied to delivery device 10. The translation of such energy is of itself, conventional and well known for example, in the dental prophylactic scaling art, and need not be further described here.

Because vibrational energy is translate to delivery device 10, the material contained therein, such as dental material 20, is caused to vibrate. This in turn cause a reduction in the viscosity of the dental material 20, sufficient to reduce its viscosity. Materials that reduce viscosity when vibrational energy is applied are known as being thixotropic. Dental material such as Dyract, Integrity, Prisma and SureFil, all available from DENTSPLY are examples of such dental materials. While all of these materials are restoratives, other dental materials as discussed above can also benefit and are therefore useful, with the present invention.

As stated, delivery device 10 can be preloaded or it can be simply a receptacle which is loaded at the time of use with an appropriate dental material 20. Preferably, delivery device 10 is a preloaded with selected material, and is also otherwise configured for application of the material. For example, delivery device 10 may be provided with a nozzle 21 configured to take advantage of the viscosity reduction imparted by the invention. This is useful in a number of ways, including that very small quantities of dental material 20 can be applied than would otherwise be possible without the present invention. Without the reduction in viscosity that the invention provides, the application of small quantities would not otherwise be possible. This allows for increased precision in application to the practitioner.

Preferably, delivery device 10 is also configured to also supply heat energy to the dental material 20. This may be accomplished by any means, such as by supplying electrical energy from generator 13 to delivery device 10 in a manner to cause delivery device 10 itself to heat. The heating may also be internal of delivery device 10. Further still, the interior walls of delivery device 10 may be heated, or a separate heating element 22 may be provided that accepts electrical energy from generator 13 and translates such electrical energy into heat energy. Heating element 22 would of course, be connected to an appropriate circuit or connector 23 for such purposes. FIG. 2 shows an alternative embodiment of Delivery device 10 wherein nozzle 21 is of a different size than nozzle 21 of FIG. 1. This will allow for a different amount and/or viscosity of dental material 20 to be applied. Further, a piston 24 and follower 25 may be employed in delivery device 10 to otherwise impart mechanical forces to dental material 20 to further induce desired movement.

According to one aspect of the invention, a delivery device 30 is configured for particular use in endodontic obturation procedures. Such procedures known in the art have included use of an obturation material on a carrier, such as the Thermafil obturator available from DENTSPLY. The obturator is placed into a suitable heating device, such as an oven, to warm the material and make it flow. The carrier is then inserted into the prepared root canal, and the material is cause to move coronally to fill the canal.

The present invention imparts both heat and vibrational energy to carrier 30 by operative connection via connector 31 to generator 32. Heat and vibrational energy are translated to carrier 30 in a manner similar to that delivered to delivery device 10. Material, such as gutta percha 33 is therefore, caused to be reduced in viscosity and to flow as desired.

According to another aspect of the invention, particularly suited for the placement of material into a tooth to be restored or for the placement of endodontic material into a root canal, a cannula 40 is employed. Cannula 40 has a passage 41 therethrough, preferably a lengthwise passage, and is operatively connected through connector 42 to a generator for imparting vibrational and heat energy in a manner substantially similar to that provided by generator 32. In this embodiment of the invention, there is also provided a material reservoir or source 50 which while shown separate from generator 43 in the drawings, may be supplied in conjunction therewith. Source 50 supplies a quantity, preferably a continuous or selectable flow of a quantity of dental material 60 to cannula 40 passage 41. By either imparting heat, vibrational energy, mechanical energy (including pressure) or some combination thereof, preferably at least heat and vibrational energy, material 60 can be caused to flow through passage 40 to be applied. This will allow the practitioner to substantially backfill the treated area while the cannula 40 is removed therefrom. Source 50 may be pressurized to help further induce flow through cannula 50. Cannula 40 may be supplied with an outer layer of material 51, such as is the case with gutta percha 33, which is used in endodontic obturation procedures. Thus the root canal is obturated and automatically backfilled at the same time.

As will be appreciated, heat, vibrational and or mechanical energy may be applied according to the present invention, either sequentially in any combination or at the same time again in any combination. It is to be further appreciated that the present invention carries out the objects thereof and otherwise provides a valuable and new contribution to the art. The invention has been described and illustrated without attempting to show all of the various embodiments that are within its scope. The scope of the invention will therefore, be determined only by any attached claims.

What is claimed is:

1. A method of applying dental materials from an application instrument to a site of application comprising the steps of:

imparting vibrational and heat energy to the dental materials to be applied through the application instrument prior to application of the dental materials to the site of application, such that a desired dental material viscosity is substantially achieved prior to application of the dental material to the site of application; and, allowing the dental materials to flow from said application instrument to the site of application, wherein the application instrument is a receptacle for the dental materials such that the application instrument directly contains the dental materials therein, and wherein the vibrational energy is imparted by a device and the heat energy is imparted by a device that are both internal to the receptacle for the dental materials.

2. A method as in claim 1 comprising the further step of curing the dental material.

3. A method as in claim 1 comprising the further step of applying mechanical forces to the dental materials.

4. A device for delivering dental material to a site in the oral cavity comprising means to impart vibrational energy and heat energy to the dental material while present in the device, wherein the device is a receptacle for the dental material such that the device directly contains the dental materials therein, and wherein the means for supplying vibrational energy and the means to impart heat energy are both intern& to the receptacle for the dental materials.

5. A method as in claim 1 wherein the vibrational and heat energy are supplied by separate elements.

6. A device as in claim 4 wherein the means to impart vibrational energy and heat energy are two separate means.

* * * * *